United States Patent [19]

Toyosu et al.

[11] Patent Number: 4,517,983
[45] Date of Patent: May 21, 1985

[54] ELECTRODE SETS WITH RESILIENTLY MOUNTED PIN ELECTRODES

[76] Inventors: Yasuhiro Toyosu, 15-5, Minamikomatsushimacho, Komatsushima-shi, Tokushima, Japan, 773; Norio Akamatsu, 1-8, Higashiyoshinocho 2-chome, Tokushima-shi, Tokushima, Japan, 770

[21] Appl. No.: 405,955
[22] PCT Filed: Jan. 4, 1982
[86] PCT No.: PCT/JP82/00001
 § 371 Date: Jul. 29, 1982
 § 102(e) Date: Jul. 29, 1982
[87] PCT Pub. No.: WO82/02333
 PCT Pub. Date: Jul. 22, 1982

[30] Foreign Application Priority Data

Dec. 31, 1980 [JP] Japan ................................ 55-187524

[51] Int. Cl.³ ............................................. A61B 5/04
[52] U.S. Cl. ................................................. 128/639
[58] Field of Search ............... 128/639, 644, 695, 696, 128/710, 712, 902

[56] References Cited

U.S. PATENT DOCUMENTS

| | | | |
|---|---|---|---|
| 3,516,400 | 6/1970 | Krohn et al. | 128/696 |
| 3,628,527 | 12/1971 | West | 128/639 |
| 4,037,590 | 7/1977 | Dohring et al. | 128/790 |
| 4,121,575 | 10/1978 | Mills et al. | 128/644 |
| 4,275,743 | 6/1981 | Hjort | 128/644 |

Primary Examiner—William E. Kamm
Attorney, Agent, or Firm—Wenderoth, Lind & Ponack

[57] ABSTRACT

An electrode for an electrocardiograph in which potentials of the human body surface near the heart are detected by electrodes, and signals from the electrodes are processed through a computer to make an isopotential map of the body. The electrodes each have a plurality of sets of pin contacts and each set includes a plurality of pin contacts. The space between pin contacts of a set is much smaller than the space between pin contact sets. Each pin contact is pushed toward the body surface separately by means of a resilient member. The pin contacts of a set are mutually electrically connected in parallel. The potential of the body surface can be accurately detected as long as one pin contact of a set is in good contact, even if the other contacts are in bad contact.

7 Claims, 11 Drawing Figures

F.I.G. 10
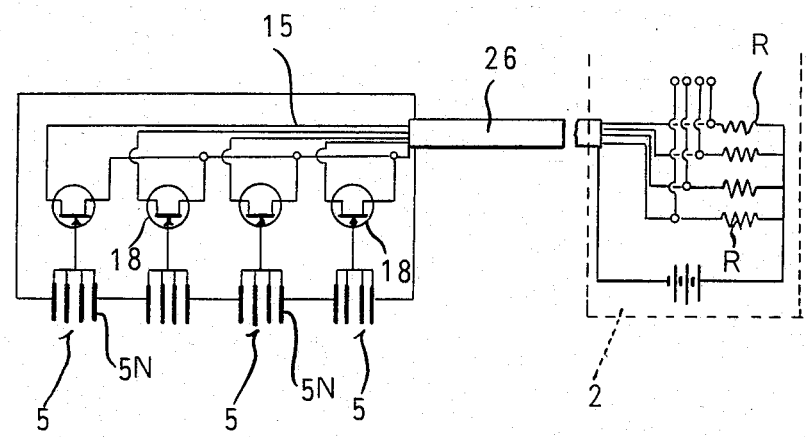
F.I.G. 11
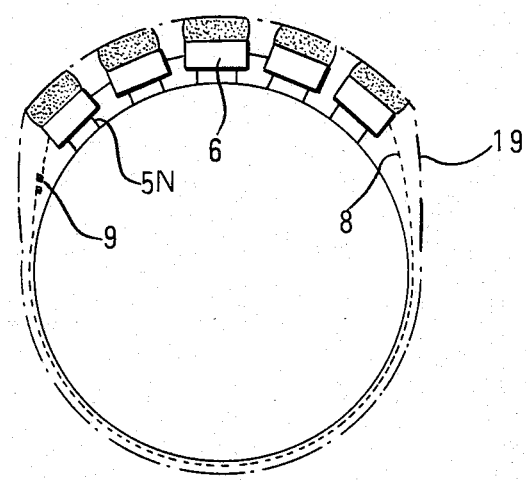

ELECTRODE SETS WITH RESILIENTLY MOUNTED PIN ELECTRODES

FIELD OF THE ART

The present invention relates to an electrode for an electrocardiograph used for measuring the potentials of a number of points of the human body surface near the heart, and through information processing of the measured potentials, a body surface potential map at the time of measurement is made so that the electrical activity of heart can be accurately detectd.

BACKGROUND OF THE INVENTION

According to a generally used electrocardiograph, the potential change of six points on the chest over a period of time is measured and represented on a graph with time as the abscissa and the potential the ordinate, whereby the heart disorder is detected from the wave form obtained relative to each point. However, with an electrocardiograph of this type, it is difficult to accurately examine the whole electrical activity of the heart. And according to a recently developed electrocardiograph, 80 to 200 electrodes are applied to various points of the body surface near the heart and the potential of each point is measured, whereby the electrical activity of the heart is synthetically judged.

By this electrocardiograph, an isopotential map for a certain time is made for the body surface near the heart, as shown in FIG. 1. In this isopotential map, the body surface potentials are shown on isopotential lines so as to make it possible to examine the distribution of the body surface potentials. This isopotential map is obtained e.g. by temporarily storing the potential of each electrode in a memory unit, calculating the isopotential points based on the potential of each electrode through a computer, and then drawing the isopotential lines e.g. at a pitch of a few tens of microvolts on a television or a XY-plotter.

When using this electrocardiograph, a plurality of isopotential maps are obtained at intervals of the sampling time and the enlargement or contraction of the positively and negatively charged parts of the body surface near the heart can be recognized from the change of the potential gradient, whereby the electrical activity of the heart is indicated.

However, in the electrocardiograph of this kind, it is difficult to apply a number of electrodes to the points of the body surface with small contact resistance, and to stably and correctly detect the potential of each point.

For example, it takes four persons as long as 30 minutes to 1 hour to correctly place the conventional suction type electrodes at about 100 points of the body surface, and only one or two patients can be examined under an hour even in the best conditions.

It is necessary that the electrodes of an electrocardiograph be applicable to any person, adult or child, male or female, having different body shapes. The electrodes must be free from errors in potential measurement due to the unevenness of the body surface or its upward and downward motion caused by the breathing. Further, the electrodes are required not to cause any terror, pain or sense of oppression to patients. Further, they must be able to be applied or removed easily and rapidly, and to be easily maintained. Furthermore, it is necessary to place the electrodes correctly relative to one another and without deviation.

In detecting the potentials of the points on the body surface, preferably all the electrodes are pressed onto the body surface with a strong force so as to stably and correctly measure the potentials at the electrode contact points. However, in an electrocardiograph for detecting the potentials of many points the human body, a number of electrodes are employed. And if the pressure applied for an electrode is 500 g and 100 electrodes are used, a force as strong as 50 kg is applied to the body in the area where it necessarily gives a strong sense of oppression to the patients. Therefore, such an electrocardiograph is extremely unsuitable for examining the heart of a patient having reduced strength.

Consequently, practically usable electrodes cannot be obtained simply by increasing the force with which the electrodes are pressed onto the body.

In a conventional electrocardiograph, since signals fed from each electrode are amplified and shown in a graph, the bad contact of electrodes can be easily recognized from the graph for the particular electrode.

However, in the improved electrocardiograph described above, an isopotential map of the body surface at the time of measurement is shown, and therefore, it is more difficult than in the conventional electrocardiograph to judge from the map whether there is bad contact of electrodes. Consequently, in order to examine the heart with a high accuracy, all the electrodes must be always in sure electrical contact with the body surface. If a conventional suction type electrode or an adhesive tape type electrode makes bad electrical contact for one second per 100 seconds, on the average one of the 100 electrodes is always in bad contact and accurate measurement cannot be performed.

It is known that an electrocardiograph which produces an isopotential map of the body surface near the heart can indicate more accurately the electrical activity of the heart than a conventional electrocardiograph which shows only the change of the voltage of the measuring point. However, with such an electrocardiograph, potentials of a large number of points on the body surface must be detected simultaneously and accurately. Since this problem has not yet been sufficiently overcome, the electrocardiograph of this type has not yet come into widespread use.

OBJECTS AND BRIEF SUMMARY OF THE INVENTION

An object of the present invention is to provide an electrode for an electrocardiograph by which the potentials of a number of points of the body surface can be stably, surely and accurately detected and the electrical activity of patients with different body shapes can be measured in a short time.

Another object of the present invention is to provide an electrode for an electrocardiograph in which even if one of the needle electrodes fails to be in sure contact with the body surface, an accurate potential distribution map can nevertheless be obtained.

A further object of the present invention is to provide an electrode for an electrocardiograph in which the force with which the needle electrode is applied to the body surface can be decreased and a potential distribution map of the body surface can be obtained without giving heavy pain and discomfort to patients.

These objects are achieved according to the invention by the provision of an electrode for an electrocardiograph which comprises a plurality of sets of pin contacts with the contacts in each set mutually closely arranged and electrically connected in parallel, the contact sets being spaced a distance much larger than the space between each two contacts in the contact sets, a resilient member engaging each pin contact and pushing it toward the human body surface separately, the pin contacts in each electrode set being arranged mutually in parallel or substantially parallel, whereby the potential of a part of the body surface is detected by a pin contact set having a plurality of pin contacts, and the potential of the part of the body surface being accurately detectable as long as any pin contact in a set is in sure contact with the body surface, even if the other pin contacts of the set are in bad contact therewith.

The above and other objects and novel features can be more readily recognized from the following explanation and the appended drawings. These drawings are only for explanation and do not limit the scope of the present invention.

BRIEF DESCRIPTION OF THE DRAWINGS

FIG. 10 is a circuit diagram of a FET which is connected to the electrodes; and

FIG. 11 is a sectional view illustrating the application of the electrodes to the body surface.

EXAMPLE OF THE INVENTION

Figure 1:
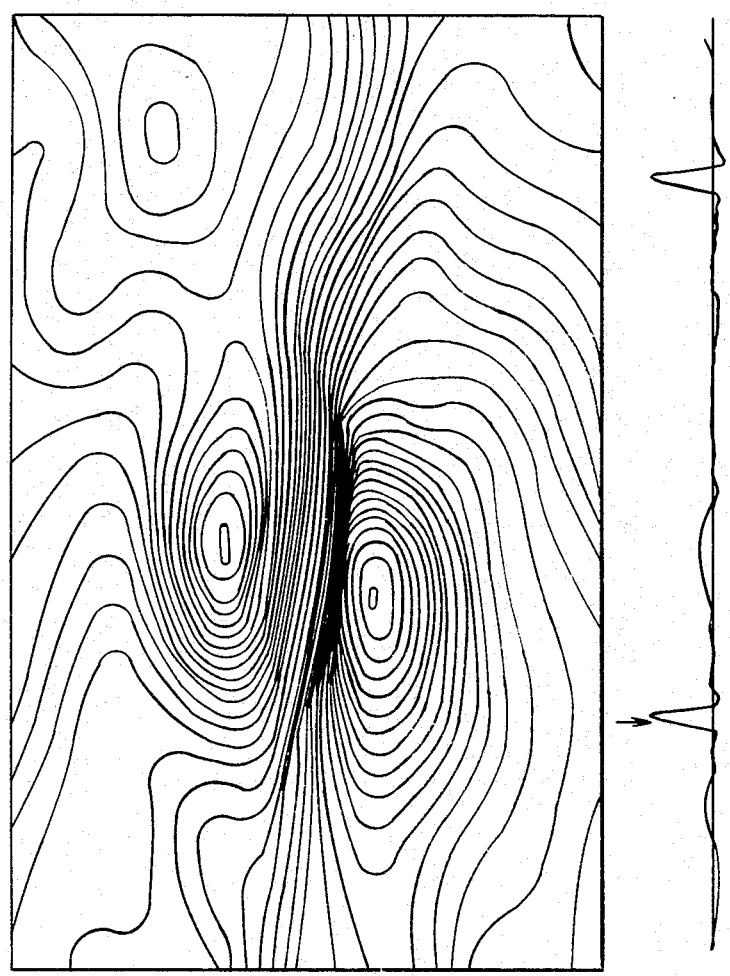
FIG. 1 is an isopotential map of the body surface near the heart.
Figure 2:
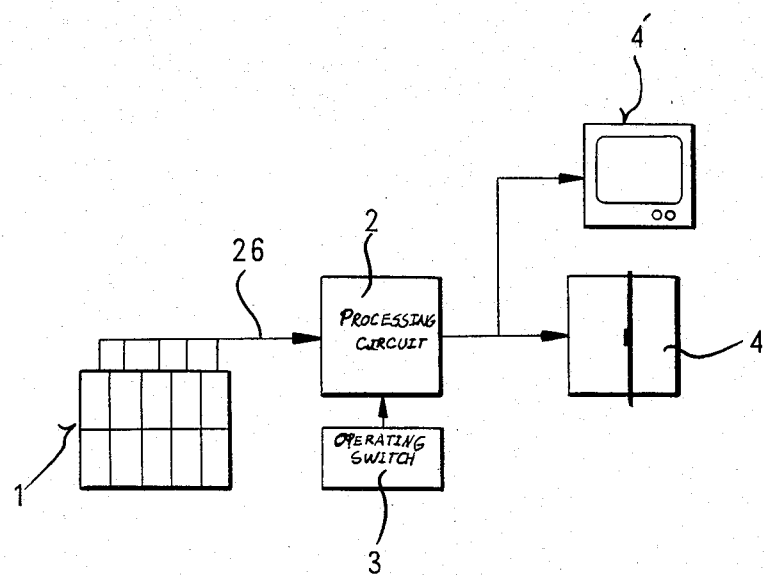
FIG. 2 is a block diagram of an example of an electrocardiograph in which an electrode according to the present invention can be used.

An electrocardiograph as shown in FIG. 2 comprises an electrode means 1, an electronic processing circuit 2, an operating switch 3, a XY-plotter 4 and a monitor 4'.

Figure 3:
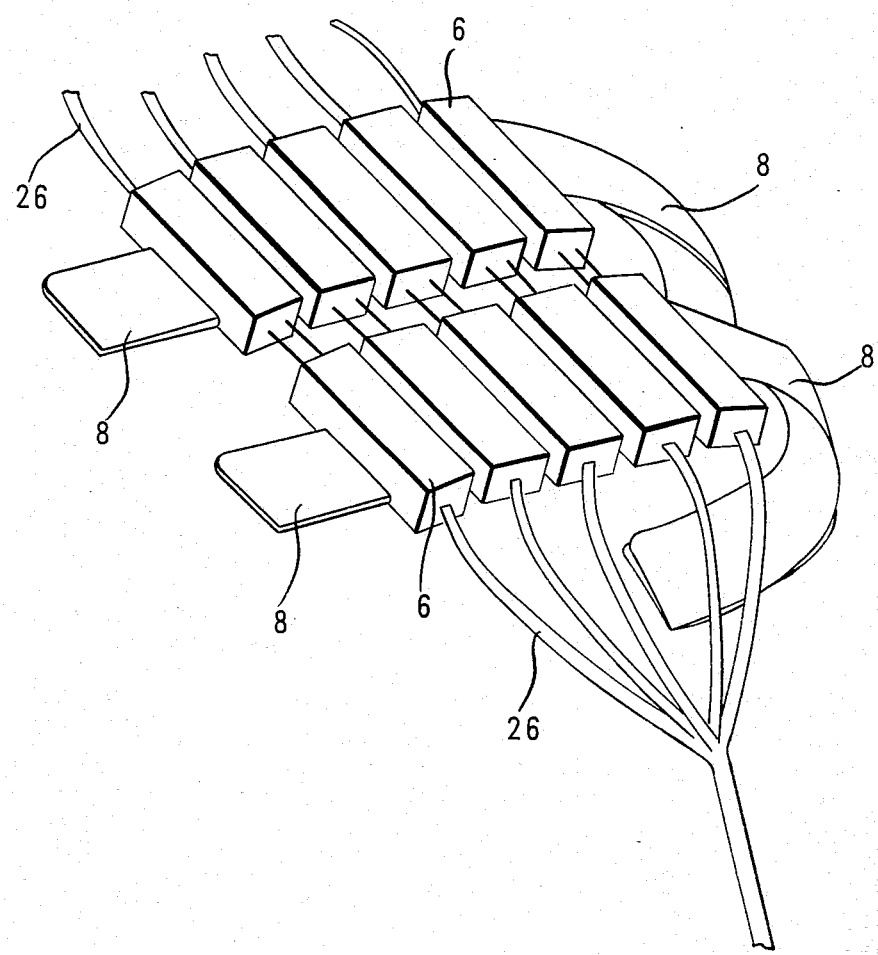
FIGS. 3 to 5 are perspective, sectional elevation and bottom views, respectively, of an example of the electrodes of the invention.
Figure 4:
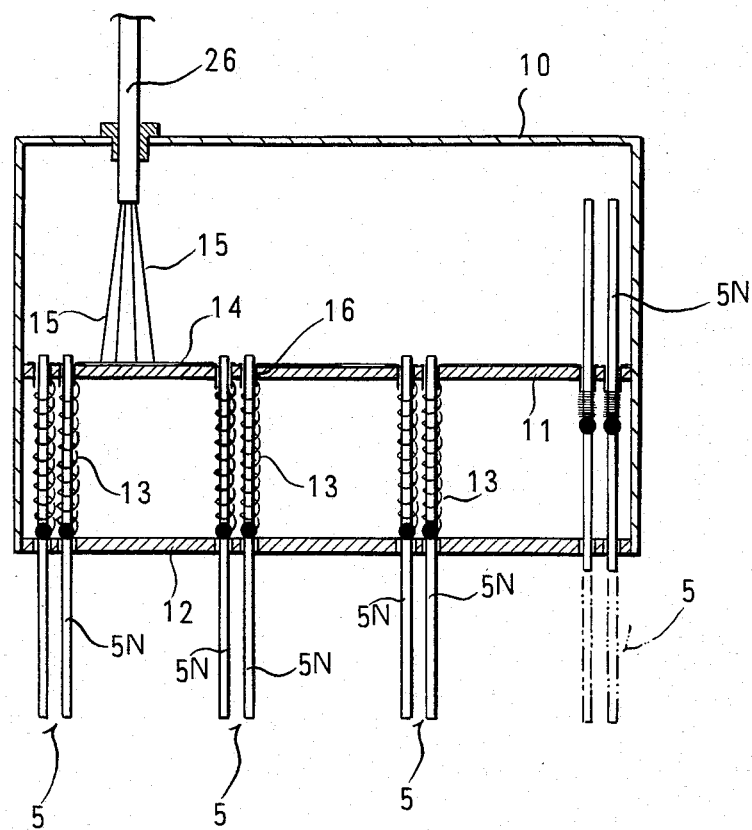
Figure 5:
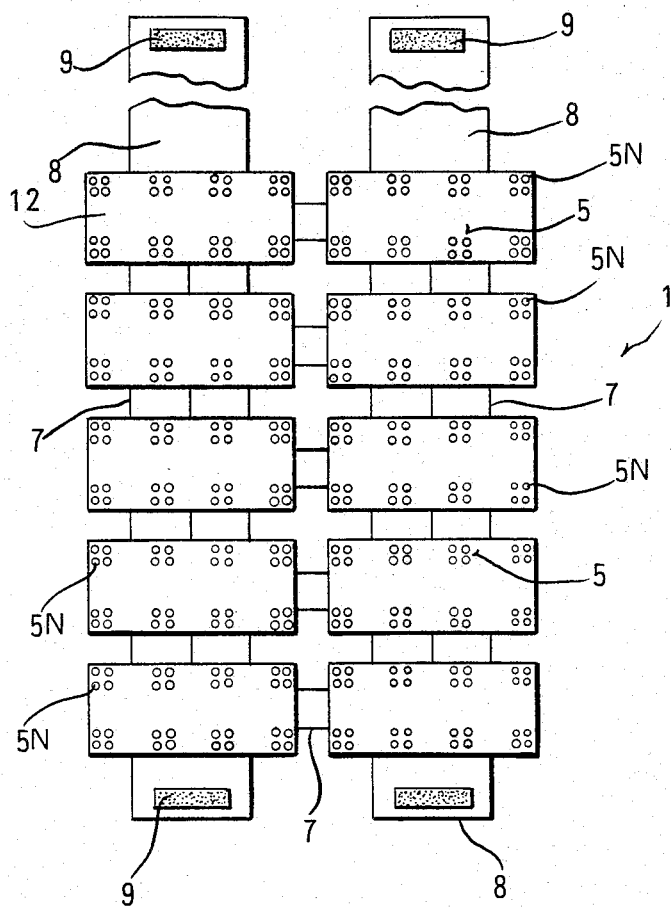

As shown in FIGS. 3 to 5, the electrode means 1 comprises ten electrode housings 6 and eight sets of pin contacts 5 mounted in each electrode housing.

The electrode housings 6 are mutually connected by a movable member 7 in the form of a string-like rubber-like elastic member. An elastic band 8 is connected to the outermost electrode housing 6, and a connecting tape 9 is sewed onto the leading edge of the band 8.

As shown in FIG. 4, the electrode box 6 is provided with the stick electrode which are arranged to be movable in the axilal direction.

The electrode housing 6 comprises a downwardly opened box-like case 10 and two electrically insulated plate members 11 and 12. Pin contacts 5N which are conductive at least on the surface thereof extend through the plate members 11 and 12 and are movable inward and outward therethrough. Coil springs 13 are provided between the plate members 11 and 12 and a pin contact 5N passes through each coil spring 13.

The coil spring 13 is a counter spring and its lower end is connected to the middle portion of the pin contact 5N and its upper end extends through the plate member 11 and is connected to a conductor printed on the upper surface of the plate member 11.

Figure 7:
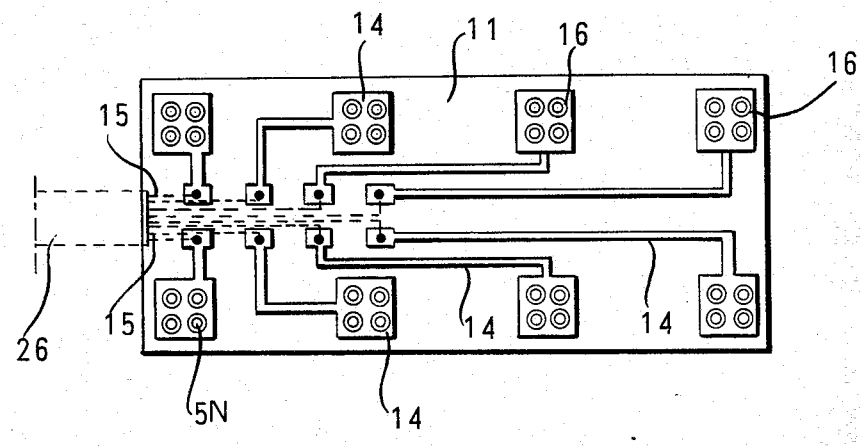
FIG. 7 is a plan view of a plate member.

Each of the electrode housings 6 shown in FIGS. 5 and 7 is provided with eight pin contact sets 5, and the total number of pin contact sets is preferably from 80 to 200. Each pin contact set is here shown as having four pin contacts 5N. The pin contact sets preferably have from two to six pin contacts.

Four pin contacts 5N are arranged close to one another. The space between the pin contacts 5N is much smaller then that between the pin contact sets. For example, the former is several to several tens of fractions of the latter. Four coil springs 13 through which the pin contacts 5N are respectively passed are connected mutually and in parallel by means of the respective conductors 14 provided on the upper surface of the plate member 11. According to this structure, even if one of the pin contacts 5N of a set 5 is out of contact with the body surface, the potential of the body surface can be detected through another pin contact 5N of the set which is in contact with the body surface. Consequently, by an electrocardiograph having electrodes of such a structure, the accurate and sure detection of the potential of the body surface is ensured.

If an electrode set comprises four pin contacts 5N, and one pin contact makes bad contact for 1 second per 100 seconds, the probability of all of four pin contacts being in bad contact at the same time is 1 per $10^8$ i.e. close to substantially zero.

According to this structure, the space between the pin contacts 5N is from 1 mm to 15 mm. The detected potential of each pin contact 5N is transmitted to a lead wire 15 through the coil spring 13 for pushing out the pin contact 5N and the corresponding conductor 14. Each pin contact 5N is movable in the axial direction independently of the movement of other pin contacts.

Figure 6:
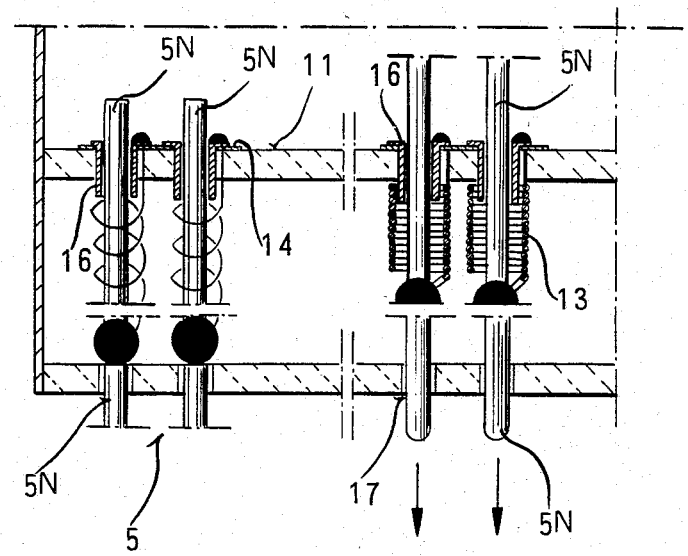
FIGS. 6, 8 and 9 are sectional views illustrating embodiments of the sets of pin contacts.

In the upper plate member 11, a tube member 16 is inserted into the through hole through which the pin contact 5N passes. The tube member 16 comprises a metal tube or a tube with an inside surface which is smooth and has low friction resistance, in order to lower the friction resistance between the tube member 16 and the pin contact 5N which is a metal wire of stainless, copper, aluminium or conductive alloy. As shown in FIG. 6, the tube member 16 extends downwardly somewhat below the lower surface of the plate member 11. The upper end of the coil spring 13 is connected to the lower end of the tube member 16 and the pin contact 5N is pushed upwardly through the tube member and the coil spring is compressed. According to this structure, when the pin electrode 5N is pushed to the uppermost position, the compressed coil spring 13 is prevented from coming into contact with the pin contact 5N and thus from restricting the movement of the pin contact 5N. Therefore, the pin contact 5N can always move smoothly through the tube member. The pin contact 5N pushed out by means of the coil spring 13 is prevented from coming out of the plate 12 by an enlarged portion on the pin contact 5N, to which the lower end of the coil spring 13 is fixed by solder or welding, and which is too large to fit through the through hole 17 in the lower plate member 12. As shown in FIG. 7, the conductors 14 of copper or the like are printed on the upper surface of the upper plate member 11 and the lead wires 15 are connected to one end of the conductors 14.

Figure 8:
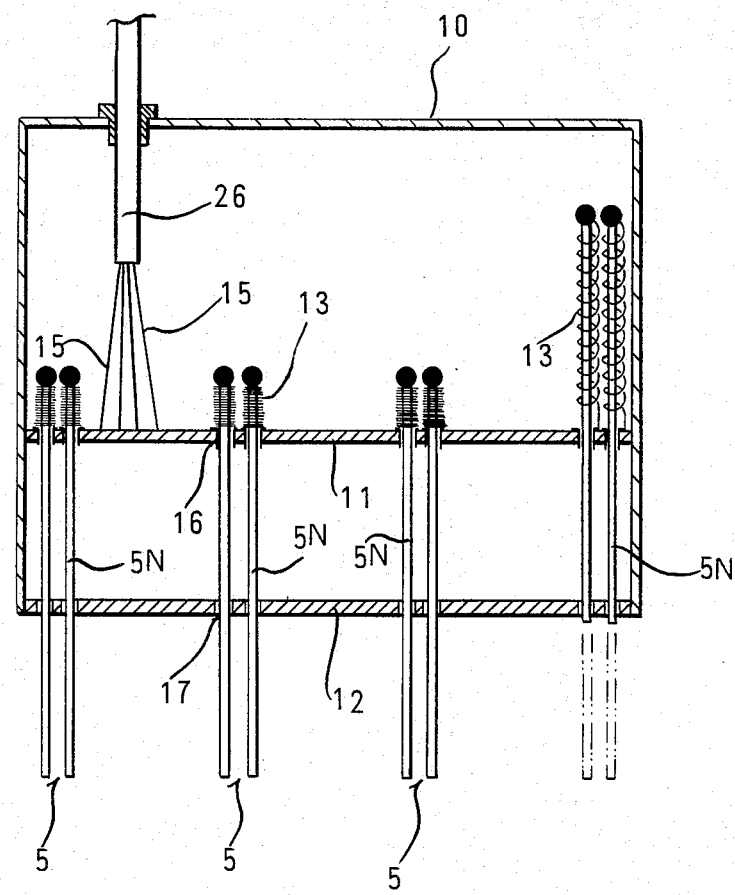

In the electrode housing shown in FIG. 8, the coil springs 13 are provided on the upper end portions of the pin contacts 5N and above the upper plate member 11. And the pin contacts 5N extend through the coil springs 13. Each coil spring 13 is a tension spring. The upper end of the coil spring 13 is connected to the upper end of the corresponding pin contact 5N and the lower end is connected to the corresponding conductor 14 printed on the surface of the plate member 11. And the lead wires 15 are connected to the respective condutors 14.

Figure 9:
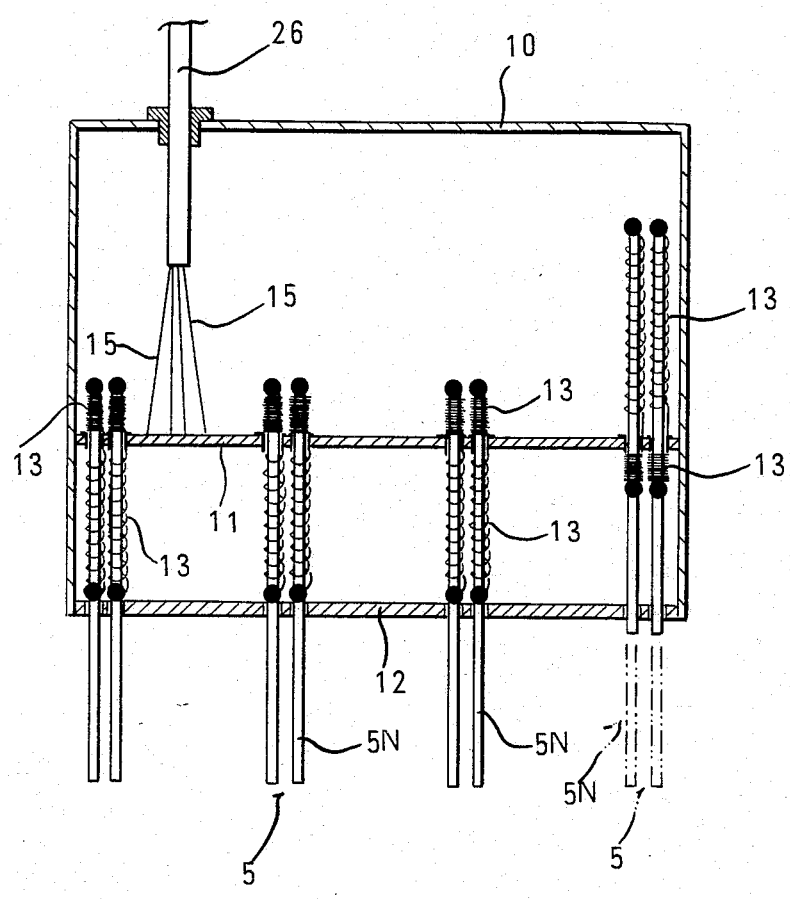

In the electrode housing shown in FIG. 9, coil springs 13 are provided above and below the upper plate member 11. According to this structure, one end of either one or both of the upper and lower coil springs is connected to the corresponding conductor 14 on the plate member 11, and the lead wires 15 are connected to the respective conductors 14. In this case, either one of the coil springs may be soft, that is, have a relatively low damping factor which indicates the power required for stretching the coil spring per a unit length.

The movable member 7 connecting the electrode housings with one another may be formed of nonelastic string or belting, or soft and elastic string or belting.

The lead wires 15 connected to the electrodes are gathered into an electrically shielded wire 26 and connected to the electronic circuit 2.

Since the potentials detected by the electrodes are rather low, attention must be paid to shielding from external noises.

For this purpose, each electrode is separately shielded whereby the ratio of S to N can be improved. In order to further lower the noise level, it is preferable that a device for amplifying the detected signal from the electrode, e.g. FET 18 be provided within the electrode housing.

The connection of FET 18 and the pin contact can be performed by providing a load resistance R for each FET 18 within the electronic circuit as shown in FIG. 10, and thus it is unnecessary to provide a power supply within each electrode housing. Further, it is convenient that the number of lead wires are not increased due to the provision of the FET. In other words, the electrode housing, having eight pin contacts, is provided with eight FET's and transmits the detected body surface potentials through eight output signal lead wires and a ground wire to the electronic circuit.

In FIG. 11, the electrodes are shown applied to the human chest surface. Each electrode housing 6 is put on the body surface near the heart, and then the two ends of the winding band 8 are connected mutually by a connecting tape 9 whereby the electrodes of the the electrode housing 6 are applied to the body surface under a given pressure. In this step, the outside of the electrode housing 6 may be further secured by an elastic band 19 so as to push the electrodes more intensely onto the body surface.

The electronic circuit 2 is adapted to perform information processing of the electrical signals transmitted from the electrodes according to a known system, for example, to calculate the isopotential curves based on the electrical signals transmitted from the electrodes at intervals of a sampling time, and then transmit the output signals therefrom to the XY-plotter 4 and the monitor scope 4' to show the isopotential maps of the body surface.

INDUSTRIAL AVAILABILITY

An electrode for an electrocardiograph according to the present invention is useful as an apparatus for detecting heart disease or detecing heart disease accompanied by other diseases in its early stages. And since, according to this invention, the time required for examining a person is very short, the operation being very easy and the parts thrown away after a measurement, such as an adhesive tape type electrode, being few and thus the cost of the measurement being low, it is especially suitable for group examination for heart disease.

What is claimed is:

1. An electrode for an electrocardiograph used for measuring potentials of a number of points of a body surface near the heart and producing an isopotential map thereof, said electrode comprising:

a plurality of pin contact sets each being conductive at least on its surface and each having a plurality of movably mounted parallel pin contacts for movement reciprocally in the direction of their lengths for directly contacting the human body surface; and resilient members, one connected to each pin contact for resiliently urging the end of each pin contact in the direction of its length toward the human body surface;

the pin contacts of each set being mounted in a small area close to one another on said electrode and being mutually electrically connected in parallel, the space between the pin contacts of each pin contact set being much smaller than the space between the adjacent small areas of the pin contact sets, whereby the potential at a position on the body surface contacted by a pin contact set can be detected as long as one pin electrode in the set is in good contact with the body, even if the other pin contacts in the set are in bad contact.

2. An electrode as claimed in claim 1 in which each pin contact set comprises two to six pin contacts.

3. An electrode as claimed in claim 1 in which each pin contact is a metal pin.

4. An electrode as claimed in claim 1 in which there are from eighty to two hundred pin contact sets.

5. An electrode as claimed in claim 1 in which the resilient member is a coil spring.

6. An electrode as claimed in claim 5 in which the coil spring for each pin contact is coiled around the pin contact and has one end electrically connected to the pin contact, and a common conductor for each set of pin contacts to which the other end of the coil springs for the pin contacts of a set are mutually electrically connected in parallel.

7. An electrode as claimed in claim 1 further comprising a preamplifier connected to said pin contacts in each set.

* * * * *